United States Patent [19]

Ryall

[11] Patent Number: 5,965,714
[45] Date of Patent: Oct. 12, 1999

[54] METHOD FOR THE COVALENT ATTACHMENT OF POLYSACCHARIDES TO PROTEIN MOLECULES

[75] Inventor: Robert P. Ryall, Stroudsburg, Pa.

[73] Assignee: Connaught Laboratories, Inc., Swiftwater, Pa.

[21] Appl. No.: 08/942,852

[22] Filed: Oct. 2, 1997

[51] Int. Cl.⁶ .............................. C07K 1/07; A61K 39/00; A61K 39/12

[52] U.S. Cl. ..................... 530/402; 530/403; 530/406; 530/391.5; 530/391.9; 424/130.1; 424/178.1; 424/184.1; 424/193.1; 424/194.1; 424/196.11; 424/197.11

[58] Field of Search ................ 530/391.1, 391.5, 530/391.9, 402, 403, 406; 424/130.1, 139.1, 178.1, 184.1, 193.1, 194.1, 196.11, 197.11

[56] References Cited

U.S. PATENT DOCUMENTS 5,425,946  6/1995  Tai et al. ............................ 424/197.11
5,565,204  10/1996 Kuo et al. ............................ 424/244.1

OTHER PUBLICATIONS

Dick. W.E. Jr. and Beurret. M. *Conjugate Vaccines. Contrib. Microbiol. Immunol.* (1989) 10. pp. 48–114. Cruse, J.M. and Lewis, R.E. Jr. eds. Basel, Karger.
Santosham, M. (1993) Vaccine 11: 552–557.
Isbell, H.S. and Frush, H.L. (1987) Carbohydrate Research 161: 181–193.
Yalpani, M. *Polysaccharides Syntheses, Modifications and Structure/Property Relations* (1988) Elsevier, Amsterdam. pp. 370–388.
Park, J.T. and Johnson, M.J. (1949) J. Biol. Chem. 181:149.

*Primary Examiner*—Ponnathapura Achutamurthy
*Attorney, Agent, or Firm*—Timothy R. Howe; G. Kenneth Smith; Connaught Laboratories Inc.

[57] ABSTRACT

Disclosed and claimed are a method for the covalent attachment of poly- and oligosaccharides to protein molecules via hydrogen peroxide depolymerization of the polysaccharide units, followed by attachment of the depolymerized polysaccharide chain to the amino acid groups of a protein of interest through a linker molecule, and products therefrom, and methods for using the products.

18 Claims, 11 Drawing Sheets

5,965,714

METHOD FOR THE COVALENT ATTACHMENT OF POLYSACCHARIDES TO PROTEIN MOLECULES

FIELD OF THE INVENTION

The present invention relates to a method for the covalent attachment of poly- and oligosaccharides to protein molecules via hydrogen peroxide depolymerization of the polysaccharide units, followed by attachment of the depolymerized polysaccharide chain to the amino acid groups of a protein of interest through a linker molecule.

Several publications are referenced in this application. Full citation to these publications is found where cited or at the end of the specification, immediately preceding the claims; and each of these publications is hereby incorporated by reference. These publications relate to the state of the art to which the invention pertains; however, there is no admission that any of these publications is indeed prior art.

BACKGROUND OF THE INVENTION

In recent years, there has been considerable interest in developing approaches to covalently attach poly and oligosaccharides to protein molecules. This approach has been applied in the area of vaccine development, where purified bacterial capsular polysaccharides have been covalently attached to protein molecules (Dick, W. E. et al., 1989). These constructs have been termed conjugate vaccines.

The reason for preparing these constructs is that purified bacterial capsular polysaccharides, which are classified as t-cell independent antigens, can be converted into t-cell-like antigens by covalent attachment to certain protein molecules. Unconjugated polysaccharide vaccines are not capable of eliciting an anamnestic response in man, and the immune response to these antigens can be of limited duration, especially in younger populations. For this reason, the polysaccharide vaccines have not been recommended for usage in infant populations, because of their inherent limited efficacy in this population.

Over the last ten to fifteen years, purified capsular polysaccharide from *Haemophilus influenzae* type b has been covalently attached to a number of protein molecules, e.g. diphtheria toxoid and tetanus toxoid protein, and these conjugates are known to elicit a t-cell dependent immune response in the infant population. This feature has allowed the development and licensure of effective vaccines against disease caused by the bacterium *Haemophilus influenzae* type b (Santosham, M., 1993). This approach of preparing conjugate vaccines has also been extended to other capsular polysaccharides, such as those purified from *Neisseriae meningitidis* and *Streptococcus pneumoniae*.

OBJECTS AND SUMMARY OF THE INVENTION

One general route that has been used to prepare these saccharide-protein conjugates is to activate one or more sites on the saccharide chain so that these activated sites will react with one or more of the protein's amino acid groups.

In developing a strategy to covalently attach polysaccharides to proteins, the present invention provides a route wherein the polysaccharide chain is initially depolymerized down to oligosaccharides of mean molecular weight in the range of 10–30,000 e.g., 10–25,000 daltons. Two advantages for using depolymerized polysaccharides to prepare the conjugates are: (a) the conjugates prepared from using depolymerized polysaccharides may be inherently more immunogenic than the corresponding conjugates prepared from full length polysaccharides; and (b) reactions used to prepare these conjugate vaccines can offer a higher degree of control, as well as more versatility in process design, when using depolymerized polysaccharide chains versus full length polysaccharide chains.

In some cases, one can covalently attach the depolymerized polysaccharide chains by adding a specific reagent that allows bond formation between the polysaccharide and protein molecules. Depending upon the chemistry that is utilized to perform this operation, one or more bonds can form between the polysaccharide and protein. In other cases, an alternative route has been employed whereby a small chemical molecule is attached to either the depolymerized polysaccharide or protein molecule, and this molecule, because of its inherent reactivity, serves as a linker molecule between the polysaccharide and protein. These molecules have been termed chemical linkers, linker and/or direct linker.

The method of the present invention preferably utilizes the latter approach, whereby a linker molecule is attached to the polysaccharide chain that affords selective attachment to protein amino acid groups. In this process, polysaccharides are first depolymerized using hydrogen peroxide under mild hydrolytic conditions. The hydrolysis reaction is a well controlled process that yields a uniform distribution of oligosaccharide chains that readily react with a hydrazide and/or an amine. The degree to which the hydrazide or amine can be attached to the hydrogen peroxide hydrolyzed polysaccharides can be increased by addition of a water soluble carbodiimide reagent compound.

The reason for this characteristic is that a certain population of the depolymerized polysaccharide chains possess a chemical group that can be readily derivatized with hydrazide or amine by the addition of water soluble carbodiimides to the reaction medium. These resulting hydrazide/amine derivatized polysaccharide chains can then be selectively attached to protein carboxylic acid groups.

Hence, the method of the present invention provides a process whereby polysaccharides can be controllably degraded or depolymerized under mild hydrolytic conditions, i.e., using low concentrations of hydrogen peroxide at slightly elevated temperatures and at slightly acidic, basic or neutral conditions, e.g., temperatures in the range of 30–80° C. and pH values in the range of 4.5–8.0±0.10.

This process was surprisingly adapted from degradation of carbohydrate molecules by alkaline hydrogen peroxide under an assortment of reaction conditions (Isbell, H. S. et al., 1987). This depolymerization process appears to proceed by a random attack at glycosidic linkages by hydrogen peroxide, thereby yielding a uniform molecular weight distribution of depolymerized carbohydrate chains.

Historically, polysaccharides have been depolymerized by a variety of approaches that include heating under either acidic, basic or neutral conditions, ultrasonic irradiation, shear force, enzyme catalyzed cleavages, radical mediated, metal-ion catalyzed, and periodate oxidation where applicable (Yalpani, M., 1988). The ability of any one of these methods to depolymerize a particular polysaccharide chain is dictated by the physical make-up of the polysaccharide chain. Prediction of the best hydrolytic conditions is, at times, difficult even when one knows the structure of the polysaccharide repeat unit.

However, in unexpected contrast to the historical approaches to depolymerizing polysaccharides, the method of the present invention has been applied to a number of structurally dissimilar polysaccharides.

Defining conditions to obtain the desired molecular weight distribution is a relatively straightforward process, because the single most influential experimental parameter in the inventive process is temperature. The other experimental parameters that allow for fine adjustments of molecular weight distribution are the percent of hydrogen peroxide used in the reaction mixture and the length of time of the reaction.

A number of mechanisms have been proposed for the alkaline degradation of carbohydrates using hydrogen peroxide (Isbell, H. S. et al., 1987). Cleavage of the chains appears to occur selectively at the glycosidic bond. The reducing end sugar so generated either remains in its native oxidation state (i.e. aldehyde) or may undergo oxidation to the next higher oxidative state (i.e. carboxylic acid). The aldehyde form is much more reactive towards hydrazides than are normal reducing end sugar groups generated by acid or base hydrolysis, which suggests that the reducing end sugar may exist in an open form and not as a hemiacetal.

According to the mechanism proposed by Isbell (1987), the reducing end sugar may undergo limited degradation in these reactions to yield a smaller alditol unit, thereby leaving the reducing end sugar in the open form. The available data supports the assertion that the chains generated by hydrogen peroxide depolymerization are much more reactive towards hydrazides than are chains that are depolymerized by either acid or base.

There are also depolymerized polysaccharide chains that contain groups that are reactive with water soluble carbodiimides, that allow for further derivatization with either amine or hydrazide containing compounds. One can derivatize both polysaccharide groups in the same reaction by adding the water soluble carbodiimide compound to the reaction medium.

Accordingly, an object of the invention can include any of providing: a method for preparing a construct, the construct comprising a poly and/or oligosaccharide covalently attached to a protein molecule, wherein the method comprises depolymerizing the poly/oligosaccharide using hydrogen peroxide under mild hydrolytic conditions, derivating the depolymerized polysaccharide and/or oligosaccharide with an amine and/or a hydrazide, preferably in the presence of a carbodiimide, and conjugating the derivatized, depolymerized oligo/polysaccharide with a protein molecule; a construct from such a method; a composition such as a therapeutic, immunological or vaccine composition comprising such a construct and optionally a pharmaceutically or verterinarily acceptable carrier or diluent; a method for making such a composition comprising the aforementioned method for preparing the construct and optionally admixing the construct with the carrier or diluent; and, a method for treating an animal (e.g., mammal) or human (including infant) in need of treatment or for inducing an immunological or protective immune response in such an animal or human comprising administering the construct or composition comprising the construct.

Therefore, the present invention provides a method for preparing a construct, the construct comprising a poly and/or oligosaccharide covalently attached to a protein molecule, wherein the method comprises depolymerizing the poly/ oligosaccharide using hydrogen peroxide under mild hydrolytic conditions, derivating the depolymerized polysaccharide and/or oligosaccharide with an amine and/or a hydrazide, and conjugating the derivatized, depolymerized oligo/polysaccharide with a protein molecule.

The invention further provides a construct derived from derivatized, depolymerized bacterial capsular polysaccharide selected from the group consisting of *Streptococcus pneumoniae* serotypes 1, 3, 4, 5, 6B, 7F, 9V, 14, 18C, 19F and 23F and *Neisseria meningitidis* groups A, C, W135 and Y.

The present invention also provides a method wherein the mean molecular weight of the depolymerized poly/ oligosaccharide is 10–30,00 daltons, e.g., 10–25,000 daltons.

The invention additionally provides a means for directly linking the derivatized, depolymerized polysaccharide and/ or oligosaccharide to a carboxylic acid group of a protein molecule using a water soluble carbodiimide reagent, which reaction may optionally be carried out in the presence of N-hydroxysuccinimide.

The invention still further provides a construct prepared according to the method of the invention wherein the construct comprises an epitope of interest, a biological response modulator and/or a growth factor, such that the present invention provides an immunological and/or vaccine or therapeutic composition comprising the construct.

The invention further comprehends methods of using the construct or composition comprising the construct; for instance by administering the construct or composition comprising the construct to an animal or human for obtaining an immunological or protective immune response or for treatment or therapy.

Still further, the invention comprehends depolymerization of poly- and/or oligosaccharides using hydrogen peroxide under mild hydrolytic conditions, e.g., (a) heating a poly- and/or oligosaccharide containing solution to 30 to 80° C. and adjusting the pH between 4.5 to 8.0±0.10; (b) adding hydrogen peroxide after the solution has reached the desired temperature; (c) heating until depolymerization is complete and cooling to room temperature; which is optionally followed by (d) neutralization of unreacted hydrogen peroxide and/or removal by ultrafiltration. In a preferred embodiment, the poly- and/or oligosaccharide concentration is approximately 1–8 mg saccharide/ml reaction volume, and the pH is between 5–8.

Additionally, the invention comprehends derivatizing the depolymerized polysaccharide and/or oligosaccharide with a molecule selected from the group consisting of an amine and a hydrazide. In a preferred embodiment, the molecule is adipic dihydrazide or 1,6-diaminohexane, the reaction is carried out in the presence of a carbodiimide, and the product of the derivatization is reduced with a mild reductant, e.g., sodium cyanoborohydride.

These and other objects and embodiments are disclosed or are obvious from and encompassed by, the following Detailed Description.

BRIEF DESCRIPTION OF THE FIGURES

FIG. 2B1–2B4 shows the reaction of hydrogen peroxide depolymerized pneumococcal 19F polysaccharide with adipic acid dihydrazide, following UV at 310 to 210 nm with time;

DETAILED DESCRIPTION OF THE INVENTION

Figure 1A:
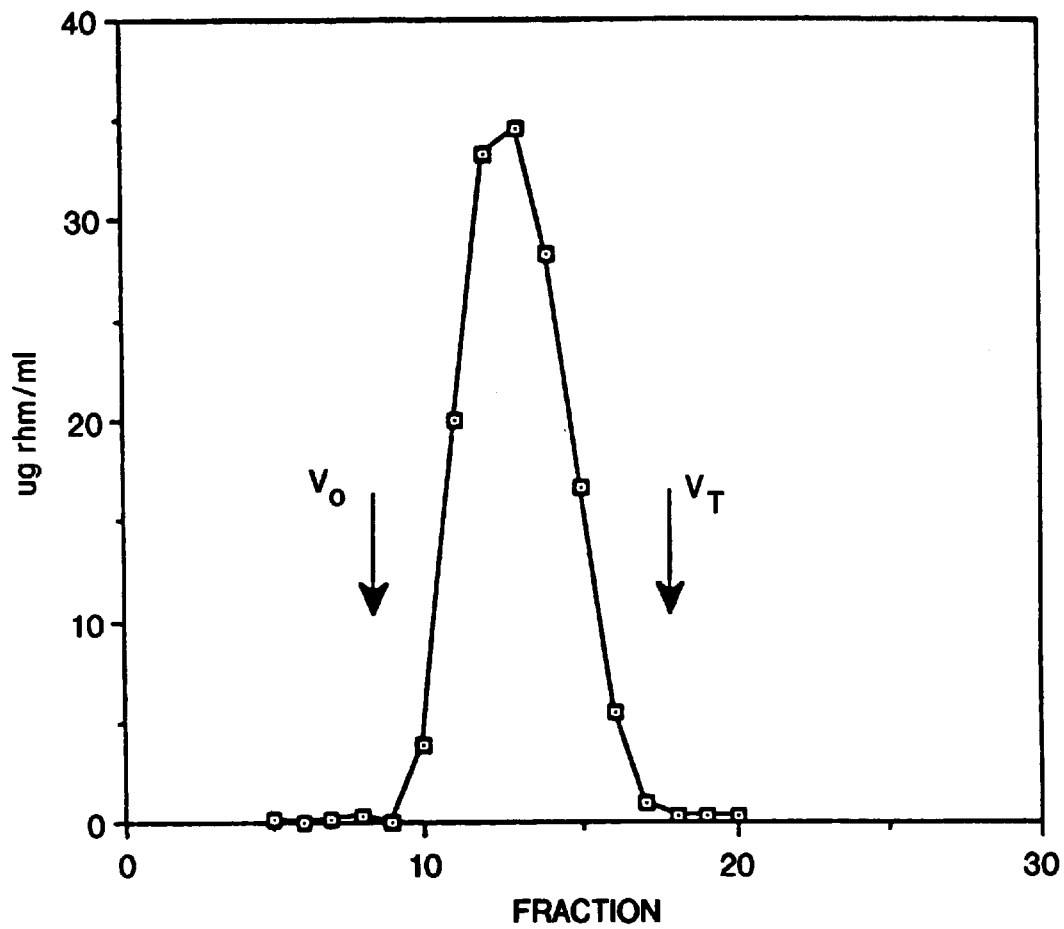
FIG. 1A shows the S-2000 SEC profile of depolymerized Pn 19F polysaccharide.
Figure 1B:
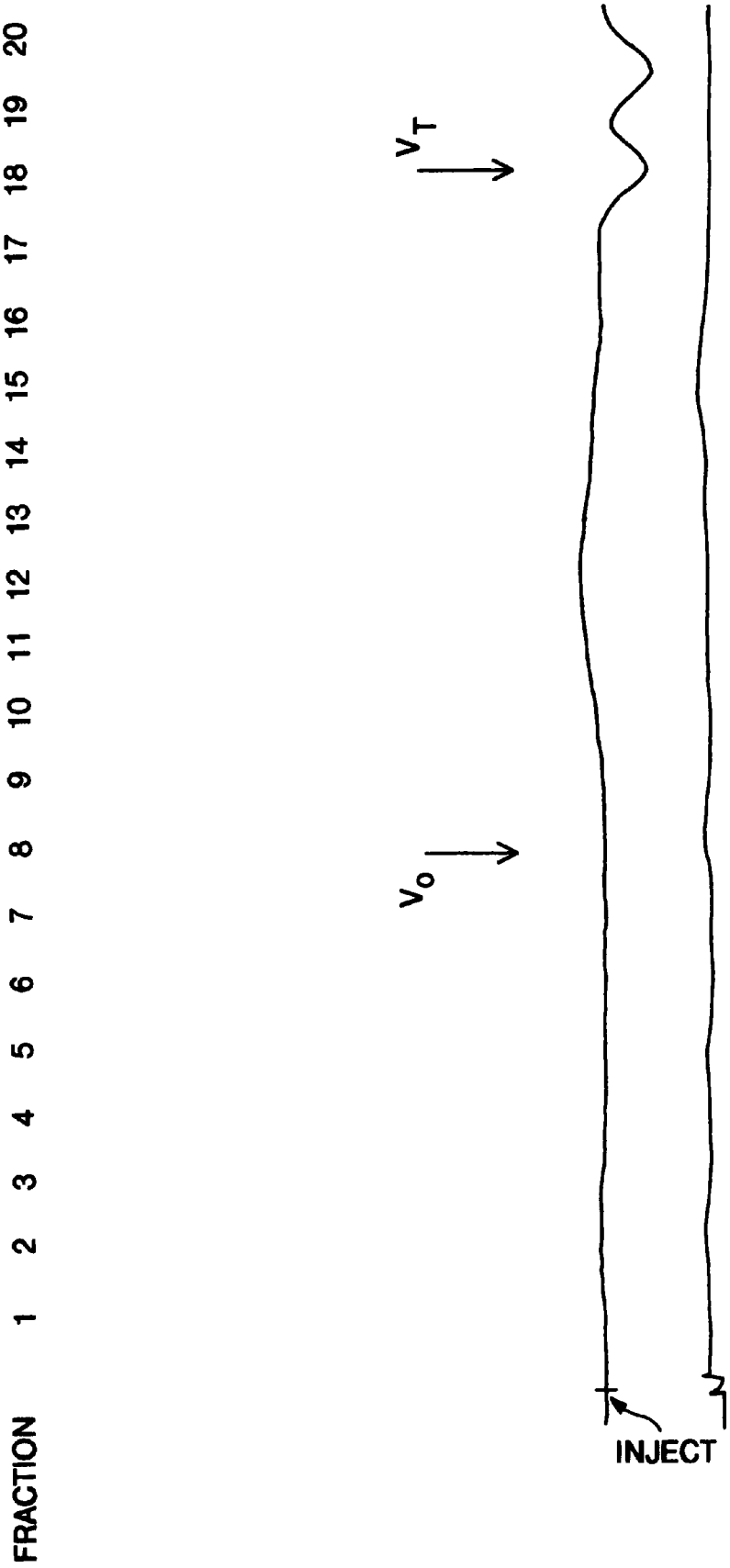
FIG. 1B shows the S-200 SEC chromatogram for depolymerized Pn 19F polysaccharide, wherein the upper tracing follows the refractive index of the sample eluent and the lower tracing follows the UV absorbance at 254 nm.
Figure 1C:
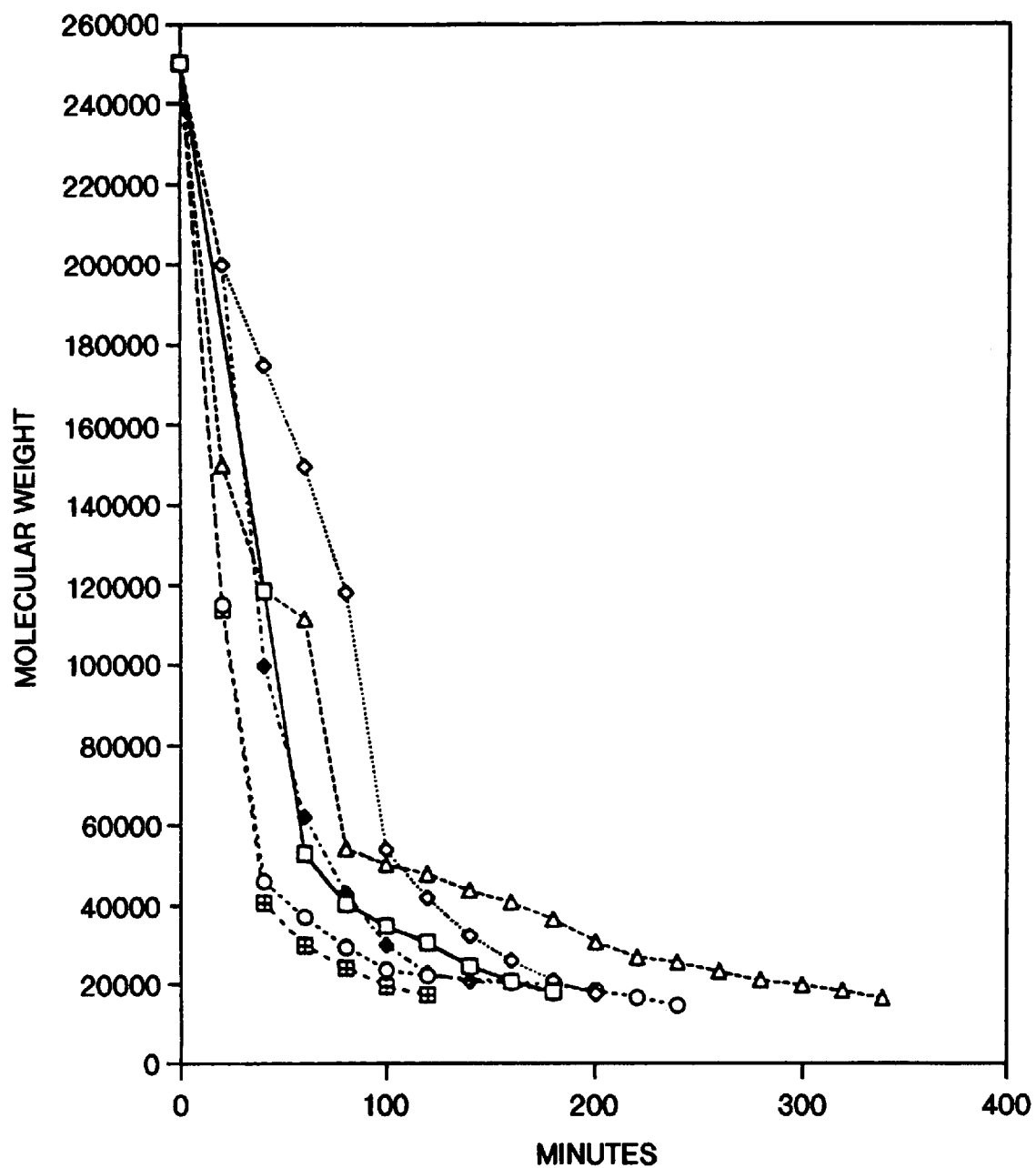
FIG. 1C shows the kinetic profile for the depolymerization of polysaccharides by hydrogen peroxide.

The inventive process has been applied to a number of distinctly different bacterial capsular polysaccharides, as well as commercially available dextran polysaccharides, although the process need not be limited to only these polysaccharides. The bacterial capsular polysaccharides that have been depolymerized and derivatized with hydrazide containing compounds by this process include *Streptococcus pneumoniae* serotypes 1, 3, 4, 5, 6B, 7F, 9V, 14, 18C, 19F, and 23F, and *Neisseria meningitidis* groups A, C, W135 and Y.

According to the method of the present invention, the polysaccharides are first dissolved in either Tris-HCl, citrate, acetate or phosphate buffer (at 50–100 mM buffer concentration), the solutions are heated to 30–80° C. and the pH is adjusted to a range between 4.5–8.0±0.1. The addition of hydrogen peroxide is made after the solution has reached the desired temperature, and this addition is taken as time zero. After the desired heating time is complete, the depolymerized material is cooled to room temperature. This step serves to stop the hydrolytic reaction. Unreacted hydrogen peroxide can be neutralized by either adding a reducing agent, such as sodium bisulfite, or by physical means of removal, e.g., dialysis or ultrafiltration.

Molecular weight determinations are made by elution through a size exclusion column that is calibrated using commercially available dextran standards. The number of reducing end groups can be determined using the Park Johnson Method (Park, J. T. et al., 1949). Recovery of polysaccharide is determined by assaying for one or more of the component sugars present in the polysaccharide repeat unit.

The kinetics of the depolymerization reaction follows a linear relationship by plotting the log mean molecular weight (MW) of the depolymerized polysaccharide versus the time that the sample is heated (reaction time). Using a series of size exclusion columns, it has been found that this linearity extends over the MW range of 10,000 to 500,000 daltons. In general, the temperature of the depolymerization reaction and the amount of peroxide used in the depolymerization reaction serve as coarse adjustments for the rate of depolymerization, i.e., the higher the temperature, or the higher the peroxide concentration, the faster the reaction.

The time of heating, or reaction time, allows for fine adjustments in achieving the desired mean molecular weight for the depolymerized polysaccharide. Polysaccharide concentration over the range of 1 to 8 mg polysaccharide/ml reaction volume does not appear to influence the outcome of the depolymerization. The pH of the depolymerization has been varied between the ranges of 5 to 8. Under a given set of reaction conditions where only the pH of the mixture is varied, the extent of depolymerization at either pH 7 or 8 is essentially the same, however, the rate of the reaction is slower at pHs below 7.

The recitation of "amine" as used herein refers to a compound of the formula $R^1NR^2R^3$, wherein $R^1$ is $C_1$ to $C_{20}$ (e.g., $C_1$–$C_{12}$, such as $C_1$–$C_8$) branched or straight chained alkyl, branched or strainght chained alkenyl, alkynyl, branched or straight chained cycloalkyl and unsubstituted or substituted aromatic (e.g., phenyl, naphthyl and phenanthryl), $R^2$ and $R^3$, independent of each other, is hydrogen, $C_1$ to $C_{20}$ (e.g., $C_1$–$C_{12}$, such as $C_1$–$C_8$) branched or straight chained alkyl, branched or straight chained alkenyl, branched or straight chained alkynyl, branched or straight chained cycloalkyl and unsubstituted or substituted aromatic (e.g., phenyl, naphthyl and phenanthryl), wherein the $C_1$ to $C_{20}$ (e.g., $C_1$–$C_{12}$, such as $C_1$–$C_8$) branched or straight chained alkyl, branched or straight chained alkenyl, branched or straight chained alkynyl, branched or straight chained cycloalkyl and unsubstituted or substituted aromatic (e.g., phenyl, naphthyl and phenanthryl) can be substituted with $NR^2R^3$, wherein $R^2$ and $R^3$ are as defined as above.

Moreover, the recitation of the term "hydrazide" refers to a compound of the formula $NH_2NR^1R^2$, wherein $R^1$ and $R^2$, independent of each other is hydrogen, $C_1$ to $C_{20}$ (e.g., $C_1$–$C_{12}$, such as $C_1$–$C_8$) branched or straight chained alkyl, branched or straight chained alkenyl, branched or straight chained alkynyl, branched or straight chained cycloalkyl, unsubstituted or substituted aromatic (e.g., phenyl, naphthyl and phenanthryl) and carbonyl, wherein the $C_1$ to $C_{20}$ (e.g., $C_1$–$C_{12}$, such as $C_1$–$C_8$) branched or straight chained alkyl, branched or straight chained alkenyl, branched or straight chained alkynyl, branched or straight chained cycloalkyl and unsubstituted or substituted aromatic (e.g., phenyl, naphthyl and phenanthryl) can be substituted with $NR^1R^2NH_2$, wherein $R^1$ and $R^2$ are as defined as above. In a preferred embodiment, the hydrazide is $NH_2NR^1C(O)R^2C(O)NR^3NH_2$, and $R^1$, $R^2$ and $R^3$ are as define above.

Figures 1, 2A:
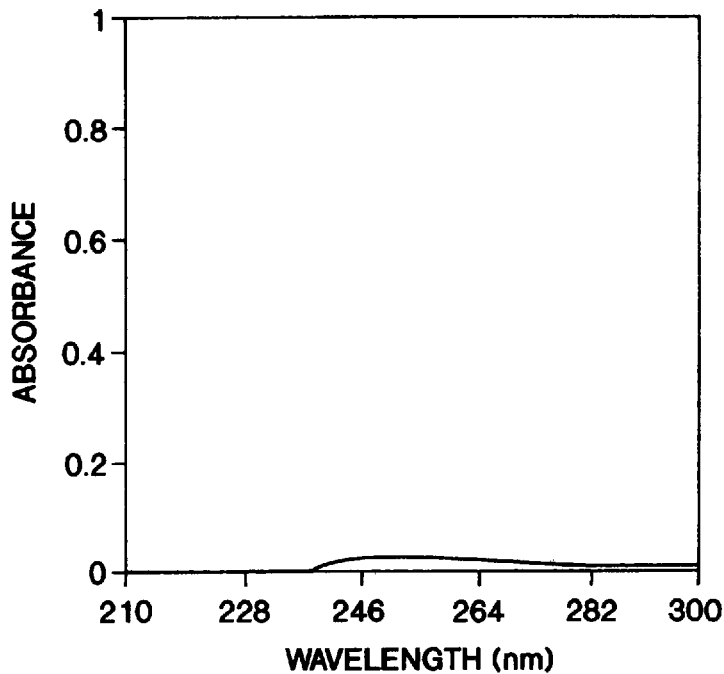
FIG. 2A1–2A4 shows the reaction of hydrogen peroxide depolymerized dextran with adipic dehydrazide, following UV at 300 and 210 nm with time.

The depolymerization reaction yields a symmetrical mean distribution of molecular weight chains, as shown in FIG. 1. All of the chains in the depolymerization reaction undergo hydrolysis, as determined by assaying for the presence of carbohydrate in the size exclusion column eluate, and the extent of depolymerization is governed by the experimental variables described herein. The recoveries of polysaccharide from the depolymerization reaction is near quantitative, which suggests that the reaction proceeds by a random cleavage of glycosidic bonds as opposed to being an end group degradation process.

The hydrolyzed polysaccharide chains are quite reactive towards amines and hydrazides. This appears to be a unique property of the inventive process, because when the same polysaccharide is depolymerized by acid or base, the resulting depolymerized polysaccharide is either unreactive or relatively slow to react with amines and hydrazides.

Figures 2, 2A:
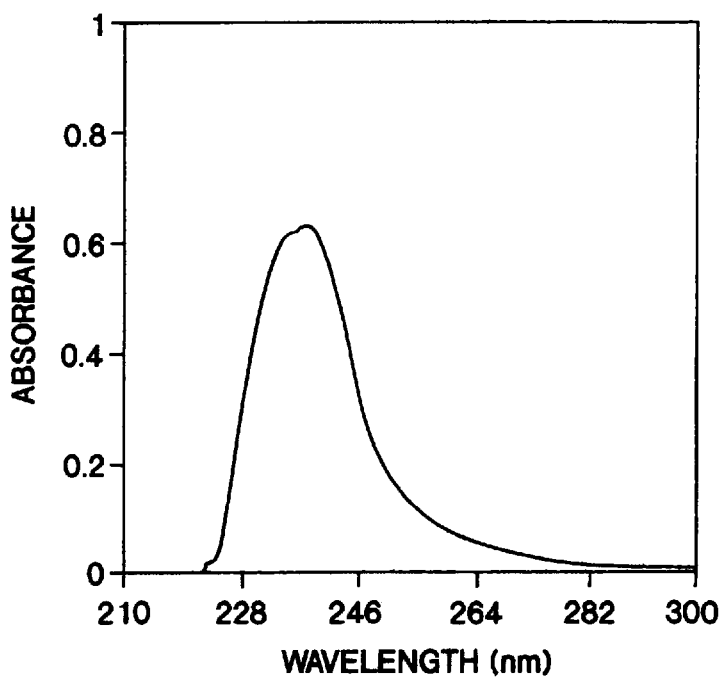
Figures 2, 2A, 3:
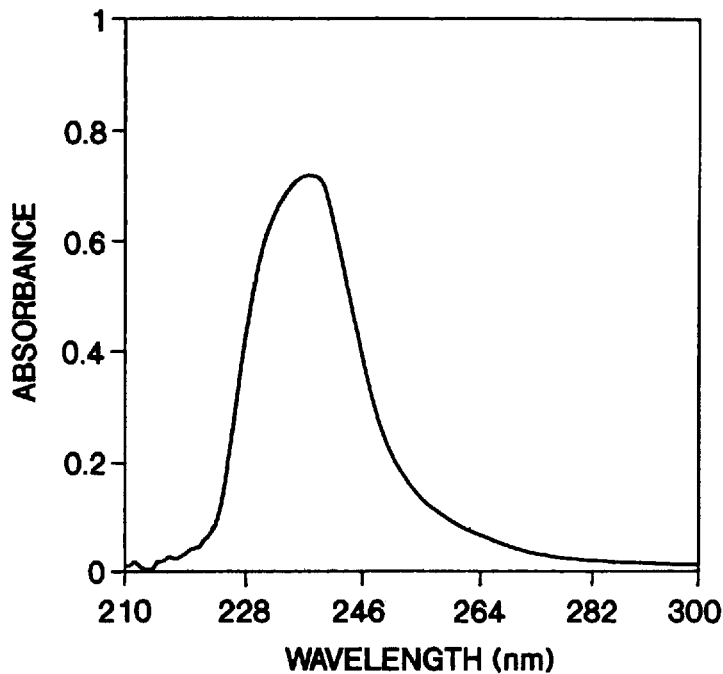
Figures 2, 2A, 3, 4:
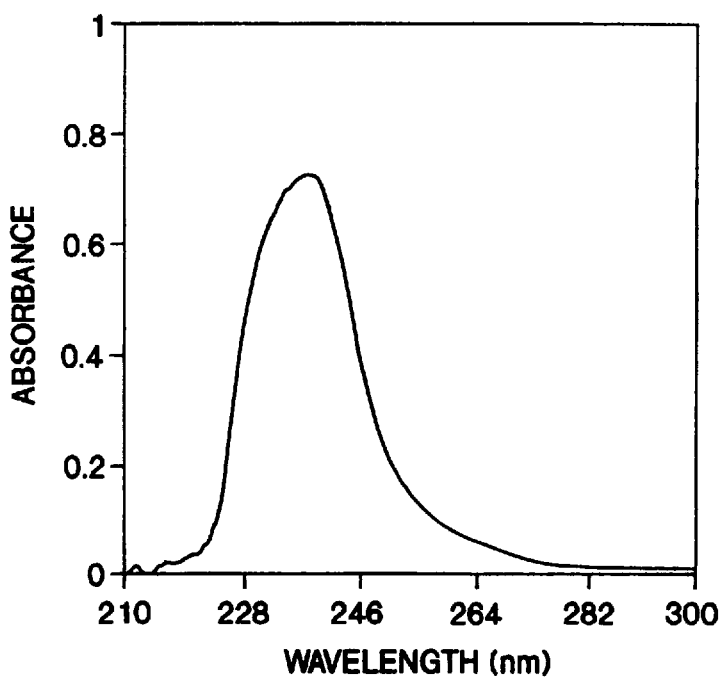
Figures 1, 2B:
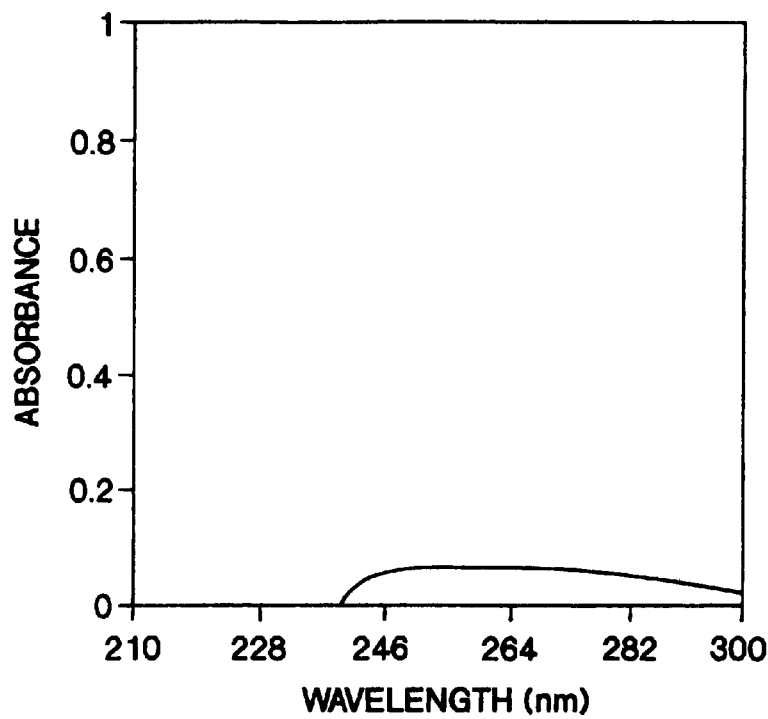
Figures 2, 2B:
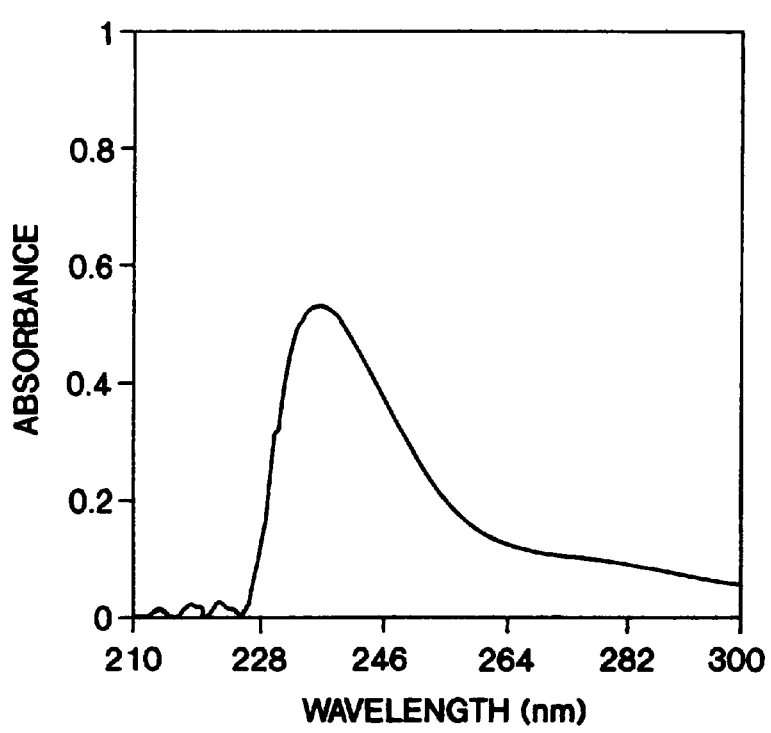
Figures 2, 2B, 3:
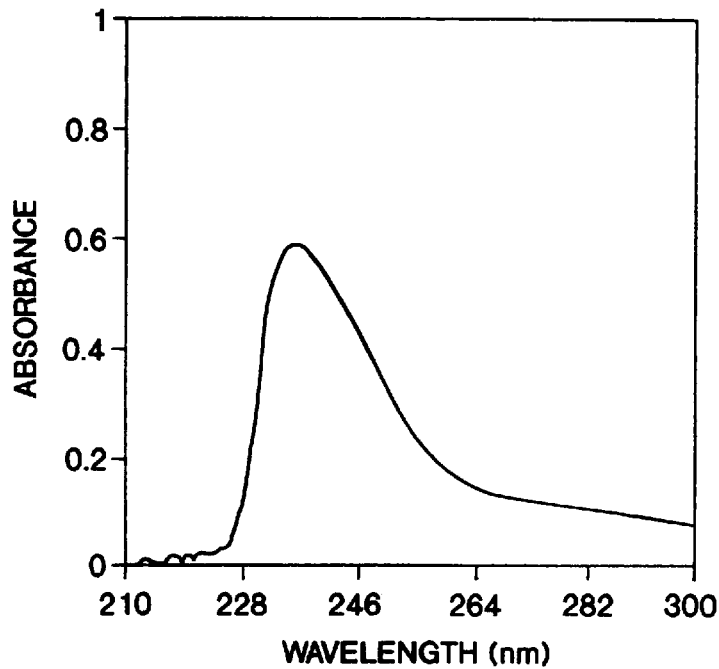
Figures 2, 2B, 3, 4:
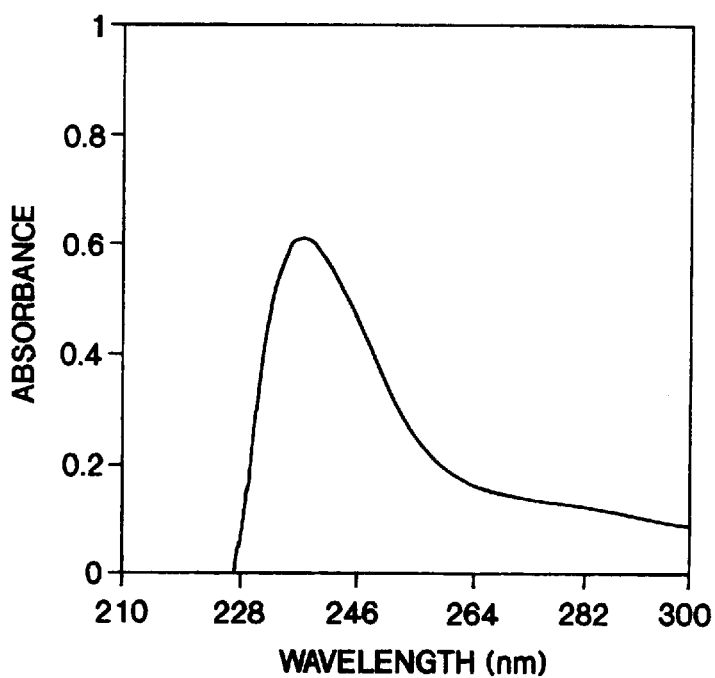
Figure 3A:
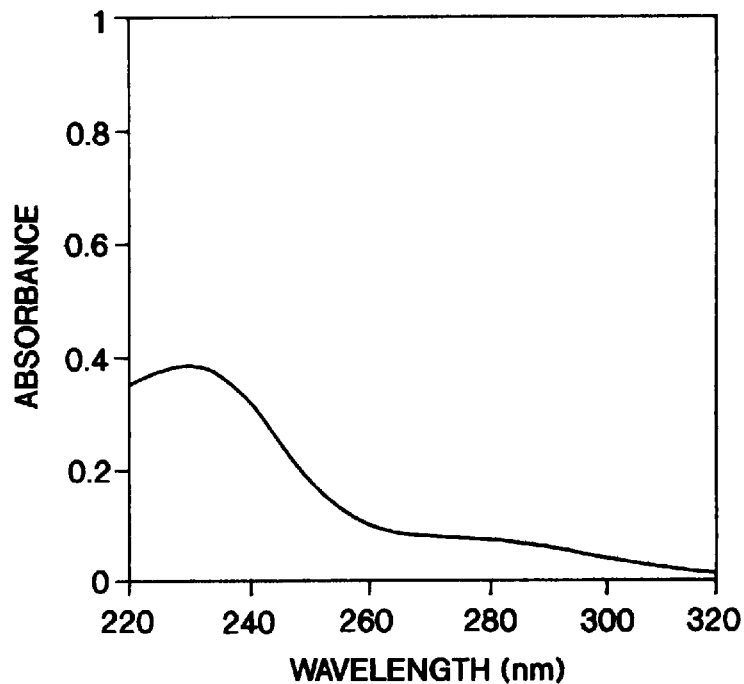
FIGS. 3A and 3B show the hydrazone formed from reaction of acetic acid hydrazide and glutaraldehyde and acetic acid hydrazide and glyceraldehyde, respectively, wherein the UV scan is from 320 to 220 nm.
Figure 3B:
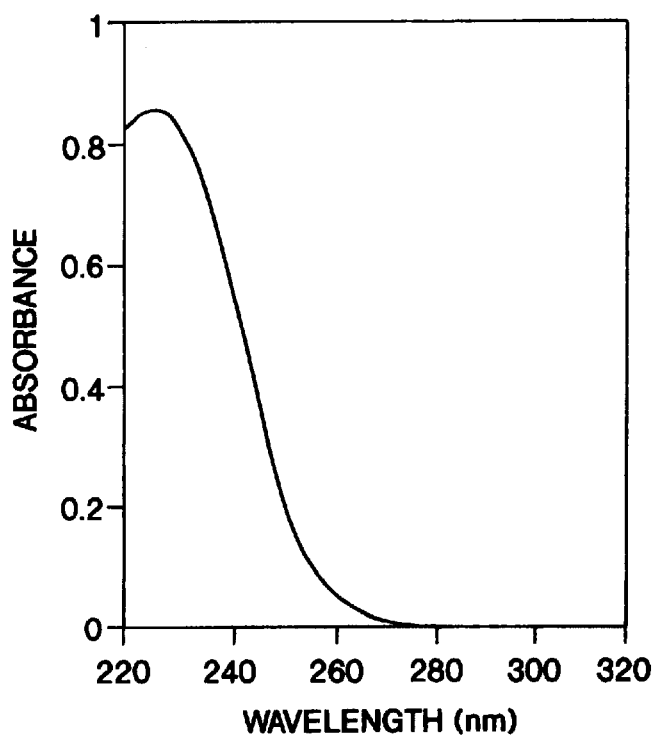

The Schiff base that forms from reacting amines with the depolymerized polysaccharides can be stabilized by reduction using sodium cyanoborohydride. The hydrazones formed from the reaction of the depolymerized polysaccharides with hydrazides are inherently much more stable than the amine generated Schiff bases formed by reacting the depolymerized polysaccharides with an amine. The hydrazones formed from the depolymerized polysaccharides with hydrazide can also be further stabilized by reduction using any appropriate reducing conditions, e.g., sodium cyanoborohydride. The reactions with either amines or hydrazides are relatively fast under the appropriate conditions. Derivatization of the depolymerized chains can be achieved within a time frame of several minutes to 1 to 2 hours, by stirring the reaction mixture at room temperature between pH 5 to 8, in an aqueous medium. These reactions can be visualized by following the increase in absorbance at 237 nm, as shown in FIG. 2. This absorbance appears to be due to the formation of hydrazone, because its $\lambda_{max}$ is approximately the same as the observed $\lambda_{max}$ for the hydrazone formed from reacting adipic dihydrazide with glutaraldehyde and glyceraldehyde, as shown in FIGS. 3a and 3b.

Additionally, there appears to be two different reactive groups that are produced as a result of the depolymerization reaction. As noted herein, one group appears to be a reactive aldehyde, based on the following observations: the depolymerized polysaccharide chains possess reducing activity when assayed by the Park Johnson method (Park, J. T., et al., 1949). The reducing activity can be eliminated when the depolymerized polysaccharide chains are treated with sodium borohydride, and the depolymerized polysaccharide chains show reactivity with reagents that are known to react with aldehydes, such as hydrazides.

The second group that is generated from these depolymerization reactions appears to be a carboxylic acid group. The carboxylic acid groups appear to arise from the oxidation of the terminal aldehyde groups during the course of the depolymerization reaction, which is in accordance with the reaction mechanisms that have been proposed (outlined herein).

The existence of the carboxylic acid group has been demonstrated as follows: when the depolymerized polysaccharide, such as dextran T-2000 or *Streptococcus pneumoniae* type 14 capsular polysaccharide, both of which are neutral, and neither of which contain a native carboxylic acid group, is first reduced with sodium borohydride, to the extent that all of the reducing activity associated with the polysaccharide is eliminated, then this reduced polysaccharide is no longer found to be reactive towards hydrazides when the two are mixed together under conditions that normally leads to reaction; however, when 1-ethyl-3-(3-dimethylaminopropyl-carbodiimide (EDAC) is included in the same reaction mixture, hydrazide is incorporated onto the reduced depolymerized polysaccharide chains. Unreduced depolymerized polysaccharide chains that are mixed with hydrazide compounds such as adipic dihydrazide or 1,6-diaminohexane will lead to reaction, whereby the hydrazides yield stable hydrazone linkages to the depolymerized polysaccharides, and the amines react to form unstable Schiff base attachments to the depolymerized polysaccharides. Both the Schiff bases and the hydrazones can be stabilized by reduction using any appropriate reducing conditions, e.g. sodium cyanoborohydride. When EDAC is included into this latter reaction, the level of hydrazide that is incorporated onto the polysaccharide chains is greater than when the reaction is performed without EDAC.

This series of results suggests that during the course of depolymerization, the chains are first cleaved in a random fashion at the glycosidic bond which yields a reducing end sugar residue. The reducing end sugar contains either an aldehyde group, or in some cases this aldehyde group undergoes further oxidation to a carboxylic acid group. The level of derivatization is consistent with each chain becoming derivatized with one reactive hydrazide or one reactive amine depending upon the co-reactant used. The theoretical level of hydrazide or amine incorporation can be determined from the molecular weight of the depolymerized polysaccharide by taking the reciprocal of the mean molecular weight, e.g. if the mean molecular weight of a given depolymerized polysaccharide is 10,000, then the theoretical maximum level of derivatization for each milligram of polysaccharide is 100 nmoles, assuming one reactive site per chain.

Figure 4A:
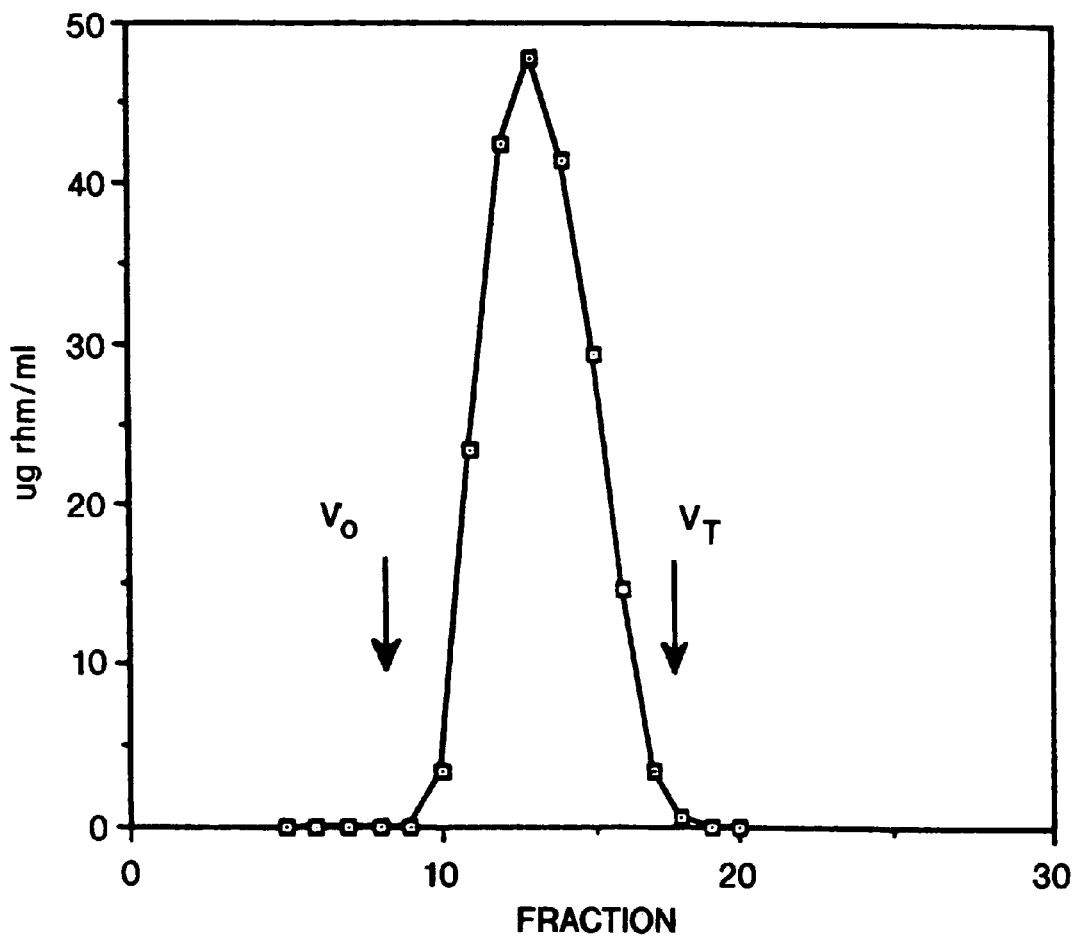
FIGS. 4A–C show the S-200 SEC profile of depolymerized and derivatized Pn6B polysaccharide, respectively.
Figure 4B:
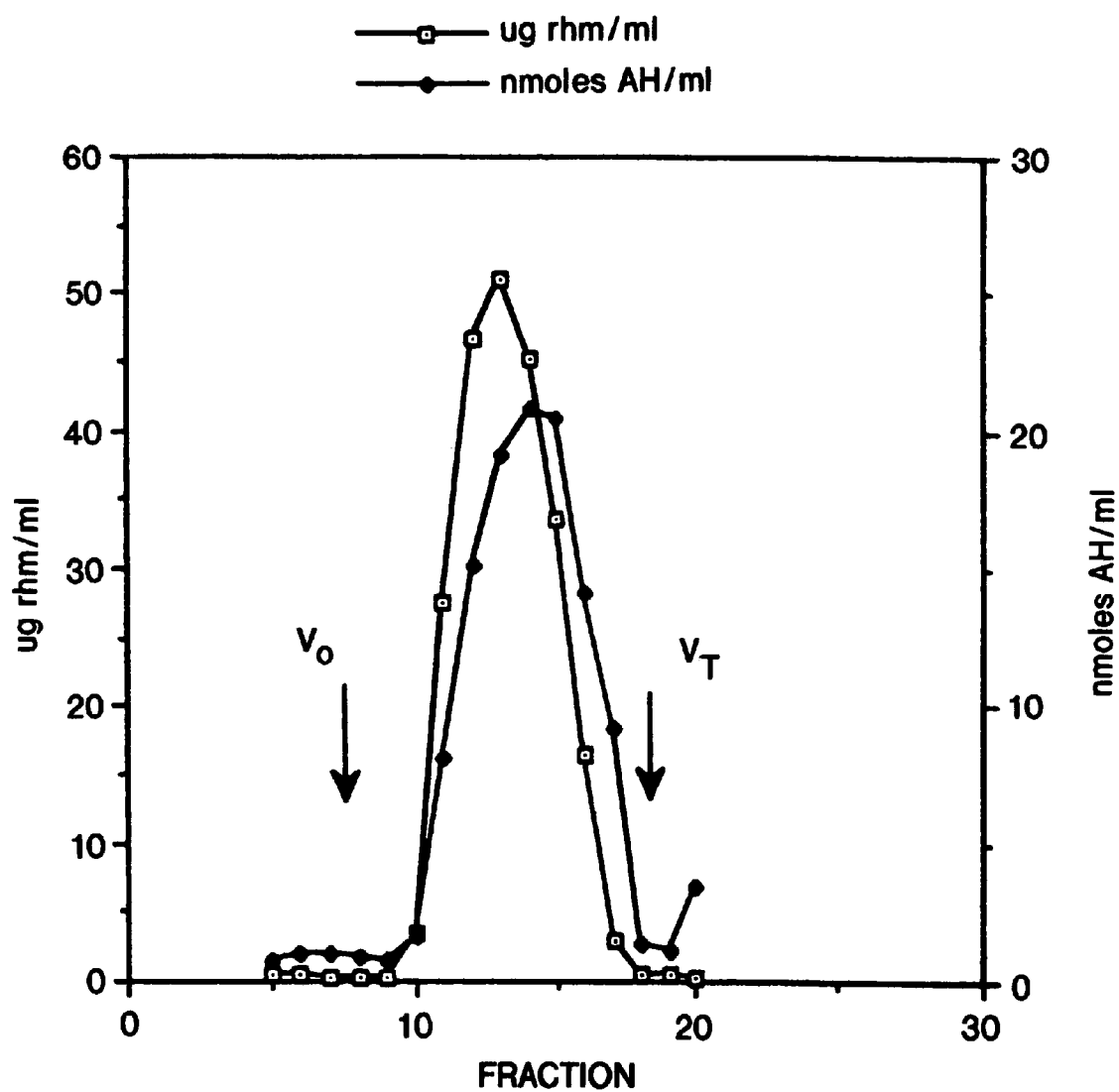
Figure 4C:
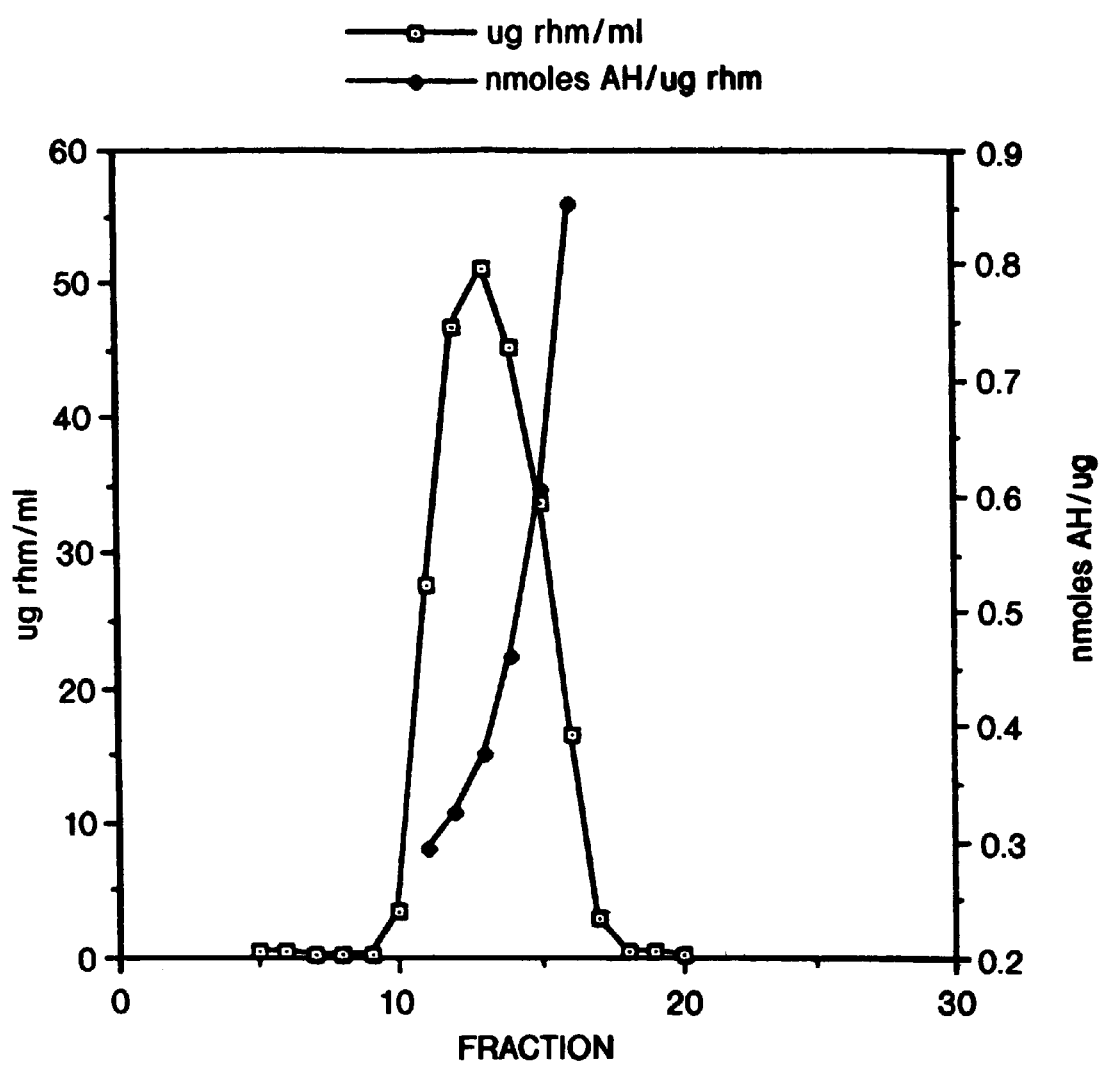

Table 1 provides a list of a number of depolymerized polysaccharides, along with their mean molecular weights, the theoretical level of hydrazide derivatization, and the observed level of derivatization. Additionally, FIG. 4a is a gel filtration chromatogram of a depolymerized polysaccharide. FIG. 4b is a second gel filtration chromatogram of the same polysaccharide after derivatization with adipic dihydrazide. As is shown in FIG. 3b, the distribution of hydrazide overlaps the molecular weight distribution for the polysaccharide. Furthermore, there is a linear relationship with respect to the level of derivatization with the molecular weight of the polysaccharide, as shown in FIG. 4c, as would be expected with a single site of derivatization per chain as opposed to a random site derivatization.

TABLE 1

Summary of the level of hydrazide derivatization for hydrogen peroxide depolymerized polysaccharides.

| Ps Type | Ps Lot | MW by SEC | nmoles AH per mg | MW by end group | Ratio of MW sec / MW e.g. |
|---|---|---|---|---|---|
| Pn3 | D01305 | 19,000 | 82 | 12,200 | 1.56 |
| Pn4 | D01306 | 17,000 | 109 | 9,200 | 1.85 |
| Pn6B | D01300 | 17,400 | 103 | 9,700 | 1.79 |
| Pn9V | D01304 | 17,000 | 90 | 11,100 | 1.53 |
| Pn14 | D01302 | 17,900 | 64 | 15,600 | 1.15 |
| Pn18C | D01038 | 18,000 | 82 | 12,200 | 1.48 |
| Pn19F | D01299 | 15,900 | 90 | 11,100 | 1.43 |
| Pn23F | D01310 | 13,900 | 125 | 8,000 | 1.74 |
| MenA | D01270 | 19,300 | 97 | 10,300 | 1.87 |
| MenC | D01741 | 19,100 | 55 | 18,200 | 1.05 |

As stated herein, the inventive process for derivatization utilizes a small molecule, e.g. adipic dihydrazide or 1,6-diaminohexane, which is covalently attached to the hydrogen peroxide depolymerized polysaccharide. These small molecules are attached to the depolymerized polysaccharide by one of two distinct bonds or linkages. In the case of adipic dihydrazide, the bond that links the small molecule to the depolymerized polysaccharide is thought to be a hydrazide linkage, that results from sodium cyanoborohydride reduction of the initial hydrazone linkage, and an acid hydrazide linkage, that results from reaction of the adipic dihydrazide reacting with the putative EDAC-activated carboxylic acid. In the case of 1,6-diaminohexane, the bond is thought to be an amine linkage, that results from sodium cyanoborohydride reduction of the Schiff base, and an amide linkage, that results from reaction of 1,6-diminohexane reacting with the putative EDAC-activated carboxylic acid. These derivatized polysaccharides are capable of readily reacting selectively with activated carboxylic acid groups, such as carbodiimide activated carboxylic acids, and N-hydroxysuccinimide esters of carboxylic acids.

Depending upon how one wishes to design the target conjugate, possessing a single selective reactive site, i.e., a site of derivatization with an amine or hydrazide, on the polysaccharide allows for a variety of choices. One can selectively connect the hydrazide or amine derivatized depolymerized polysaccharide directly to the protein carboxylic acid groups, using either EDAC or EDAC in the presence of N-hydroxysuccinimide. Alternatively, one can further derivatize the hydrazide or amine derivatized depolymerized polysaccharide with other activated small molecules, such as commercially available bifunctional linkers (i.e., any chemical molecule having two distinct reactive moieties each capable of forming a bond with a protein and/or an amino acid), and this will allow for reaction with other groups on the protein such as amino and/or thiol groups.

Additionally, it is well within the understanding of the skilled artisan to choose the appropriate reaction conditions to practice the instant invention, given the general guidelines provided herein, i.e., specifically with respect to the choice of polysaccharide and protein of interest, reducing agents, buffer conditions and appropriate linking moieties, without departing from the spirit of scope of the invention.

The polysaccharide and/or protein to which it is to be attached preferably contains one or more of the following: an epitope of interest, a biological response modulator or a growth factor. With respect to these terms, reference is made to the following discussion, and generally to Kendrew, THE ENCYCLOPEDIA OF MOLECULAR BIOLOGY (Blackwell Science Ltd., 1995) and Sambrook, Fritsch and Maniatis, Molecular Cloning, A Laboratory Manual, 2nd Ed., Cold Spring Harbor Laboratory Press, 1982.

An epitope of interest is an immunologically relevant region of an antigen or immunogen or immunologically active fragment thereof, e.g., from a pathogen or toxin of veterinary or human interest. An epitope of interest can be prepared from an antigen of a pathogen or toxin, e.g., an antigen of a human pathogen or toxin, or from another antigen or toxin which elicits a response with respect to the pathogen, such as, for instance: a Morbillivirus antigen, e.g., a canine distemper virus or measles or rinderpest antigen such as HA or F; a rabies glycoprotein, e.g., rabies glycoprotein G; influenza antigen, e.g., influenza virus HA or N or an avian influenza antigen, e.g., turkey influenza HA, Chicken/Pennsylvania/1/83 influenza antigen such as a nudeoprotein (NP); a bovine leukemia virus antigen, e.g., gp51,30 envelope; a Newcastle Disease Virus (NDV) antigen, e.g., HN or F; a feline leukemia virus antigen (FeLV), e.g., FeLV envelope protein; RAV-1 env; matrix and/or preplomer of infectious bronchitis virus; a Herpesvirus glycoprotein, e.g., a glycoprotein from feline herpesvirus, equine herpesvirus, bovine herpesvirus, pseudorabies virus, canine herpesvirus, HSV, Marek's Disease Virus, Epstein-Barr or cytomegalovirus; a flavivirus antigen, e.g., a Japanese encephalitis virus (JEV) antigen, a Yellow Fever antigen, or a Dengue virus antigen; a malaria (Plasmodium) antigen, an immunodeficiency virus antigen, e.g., a feline immunodeficiency virus (FIV) antigen or a simian immunodeficiency virus (SIV) antigen or a human immunodeficiency virus antigen (HIV); a parvovirus antigen, e.g., canine parvovirus; an equine influenza antigen; an poxvirus antigen, e.g., an ectromelia antigen, a canarypox virus antigen or a fowlpox virus antigen; an infectious bursal disease virus antigen, e.g., VP2, VP3, VP4; a Hepatitis virus antigen, e.g., HBsAg; a Hantaan virus antigen; a *C. tetani* antigen; a mumps antigen; a pneumococcal antigen, e.g., PspA; a Borrelia antigen, e.g., OspA, OspB, OspC of Borrelia associated with Lyme disease such as *Borrelia burgdorferi, Borrelia afzelli* and *Borrelia garinii*; or a chicken pox (varicella zoster) antigen. Thus, the protein and/or polysaccharide can be an antigen or immunogen, or an epitope-containing portion thereof. It is currently preferred to employ an epitope of interest from *Haemophilus influenzae* type b, *Neisseriae meningitidis* and *Streptococcus pneumoniae*.

As to epitopes of interest, one skilled in the art can determine an epitope or immunodominant region of a peptide or polypeptide from the knowledge in the art, without undue experimentation.

For instance, an epitope of interest can be generated from knowledge the amino acid and corresponding DNA sequences of the peptide or polypeptide, as well as from the nature of particular amino acids (e.g., size, charge, etc.) and the codon dictionary, without undue experimentation. See, e.g., Ivan Roitt, *Essential Immunoloqy*, 1988; Kendrew, supra; Janis Kuby, *Immunology*, 1992 e.g., pp. 79–81. Some guidelines in determining whether a protein is an epitopes of interest which will stimulate a response, include: Peptide length—the peptide should be at least 8 or 9 amino acids long to fit into the MHC class I complex and at least 13–25 amino acids long to fit into a class II MHC complex. This length is a minimum for the peptide to bind to the MHC complex. It is preferred for the peptides to be longer than these lengths because cells may cut peptides. The peptide should contain an appropriate anchor motif which will enable it to bind to the various class I or class II molecules with high enough specificity to generate an immune response (See Bocchia, M. et al, *Specific Binding of Leukemia Oncogene Fusion Protein Pentides to HLA Class I Molecules*, Blood 85:2680–2684; Englehard, VH, *Structure of peptides associated with class I and class II MHC molecules* Ann. Rev. Immunol. 12:181 (1994)). This can be done, without undue experimentation, by comparing the sequence of the protein of interest with published structures of peptides associated with the MHC molecules. Thus, the skilled artisan can ascertain an epitope of interest by comparing the protein sequence with sequences listed in the protein data base.

Even further, another method is simply to generate portions of a protein of interest, generate monoclonal antibodies to those portions of the protein of interest, and then ascertain whether those antibodies inhibit growth in vitro of the pathogen from which the from which the protein was derived.

Accordingly, the skilled artisan can use guidelines set forth in this disclosure and in the art for generating portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid sequence of an epitope of interest for obtaining a T cell, B cell and/or antibody response for use in the practice of the invention. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

With respect to a biological response modulator, reference is made to Wohlstadter, "Selection Methods," WO 93/19170, published Sep. 30, 1993, and the documents cited therein, incorporated herein by reference. The skilled artisan can obtain a biological response modulator for use in the invention, without any undue experimentation.

A growth factor can be defined as multifunctional, locally acting intercellular signalling peptides which control both ontogeny and maintenance of tissue and function (see Kendrew, supra, especially at page 455 et seq.). The skilled artisan can obtain a growth factor for use in the invention, without any undue experimentation.

As to the constructs of the invention, it should be understood that techniques for protein purification can be employed in the practice of the invention, and such techniques, in general, include standard techniques of protein purification for further purification of the protein of interest, including: precipitation by taking advantage of the solubility of the protein of interest at varying salt concentrations, precipitation with organic solvents, polymers and other materials, affinity precipitation and selective denaturation; column chromatography, including high performance liquid chromatography (HPLC), ion-exchange, affinity, immunoaffinity or dye-ligand chromatography; immunoprecipitation and the use of gel filtration, electrophoretic methods, ultrafiltration and isoelectric focusing. Each of the above-identified methods are well within the knowledge of the skilled artisan, and no undue experimentation is required to purify the constructs of the invention, using the standard methodologies outlined herein, and in the literature, as well as the teachings in the Examples below.

The invention further relates to an immunogenic, immunological or vaccine composition containing the inventive construct and optionally an acceptable carrier or diluent (e.g., veterinarily acceptable or pharmaceutically acceptable). An immunological composition containing the construct elicits an immunological response—local or systemic. The response can, but need not be protective. An immunogenic composition likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a vertebrate comprising administering to the vertebrate an inventive construct or an immunogenic, immunological or vaccine composition comprising the inventive construct and an acceptable carrier or diluent. For purposes of this specification, "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

As to antigens for use in vaccine or immunological compositions, reference is made to the documents cited herein, the discussion set forth in the documents cited herein and the knowledge in the art, e.g., Stedman's Medical Dictionary (24th edition, 1982, e.g., definition of vaccine (for a list of antigens used in vaccine formulations; such antigens or epitopes of interest from those antigens can be used in the invention, as either a construct alone, or in a multivalent composition containing at least one inventive construct).

When the construct comprises a growth factor and/or biological response modulator, the invention a therapeutic composition containing the inventive construct and optionally an acceptable carrier or diluent (e.g., veterinarily acceptable or pharmaceutically acceptable), and a method for treating a vertebrate, animal or human in need of treatment comprising administering the construct or composition comprising the construct to the vertebrate, animal or human. Further, as immunological, antigenic, immunogenic or vaccine compositions are now being used in therapies, the invention comprehends a therapeutic composition containing the inventive construct comprising an epitope of interest and optionally an acceptable carrier or diluent (e.g., veterinarily acceptable or pharmaceutically acceptable), and a method for treating a vertebrate, animal or human in need of treatment comprising administering the construct or composition comprising the construct to the vertebrate, animal or human.

The administration procedure for the inventive constructs, compositions of the invention such as immunological, antigenic or vaccine compositions or therapeutic compositions can be via a parenteral route (intradermal, intramuscular or subcutaneous). Such an administration enables a systemic immune response. The administration can be via a mucosal route, e.g., oral, nasal, genital, etc. Such an administration enables a local immune response.

More generally, the inventive antigenic, immunological or vaccine compositions or therapeutic compositions can be prepared in accordance with standard techniques well known to those skilled in the pharmaceutical, medical or veterinary arts. Such compositions can be administered in dosages and by techniques well known to those skilled in the medical or veterinary arts taking into consideration such factors as the breed or species, age, sex, weight, genetics and condition of the particular patient, and the route of administration. The compositions can be administered alone, or can be co-administered or sequentially administered with other compositions of the invention or with other immunological, antigenic or vaccine or therapeutic compositions. Such other compositions are administered taking into account the aforementioned factors.

Examples of compositions of the invention include liquid preparations for orifice (e.g., oral, nasal, anal, genital, e.g., vaginal, etc.) administration such as suspensions, syrups or elixirs; and, preparations for parenteral, subcutaneous, intradermal, intramuscular or intravenous administration (e.g., injectable administration) such as sterile suspensions or emulsions. In such compositions the construct may be in admixture with a suitable carrier, diluent, or excipient such as sterile water, physiological saline, glucose or the like.

Antigenic, immunological or vaccine compositions typically can contain an adjuvant and an amount of the construct to elicit the desired response. In human applications, alum (aluminum phosphate or aluminum hydroxide) is a typical adjuvant. Saponin and its purified component Quil A, Freund's complete adjuvant and other adjuvants used in research and veterinary application. Chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, NH) can also be used.

The composition may be packaged in a single dosage form for immunization or treatment by parenteral (e.g., intramuscular, intradermal or subcutaneous) administration or orifice administration, e.g., perlingual (e.g., oral), intragastric, mucosal including intraoral, intraanal, intravaginal, and the like administration. And again, the effective dosage and route of administration are determined by the nature of the composition, by the nature of the construct, and by known factors, such as breed or species or race, age, sex, weight, gentics condition and nature of the vertebrate or animal or human, as well as $LD_{50}$ and other screening procedures which are known and do not require undue experimentation. Dosages of construct can range from a few to a few hundred micrograms, e.g., 5 to 500 μg.

Suitable carriers or diluents can be water or a buffered saline, with or without a preservative. The construct may be lyophilized for resuspension at the time of administration or can be in solution. The carrier may also be a polymeric delayed release system. See, e.g., Kreuter, J., *Microcapsules and Nanoparticles in Medicine and Pharmacology*, M. Donbrow (Ed). CRC Press, p. 125–148. Microencapsulation has been applied to the injection of microencapsulated pharmaceuticals to give a controlled release. Examples of useful polymers for microencapsulation are polycarbonates, polyesters, polyurethanes, polyorthoesters and polyamides, particularly those that are biodegradable.

A carrier for controlled release can also be poly (d,1-lactide-co-glycolide) (PLGA). See, e.g., Eldridge, J. H., et al. *Current Topics in Microbiology and Immunology*, 1989, 146:59–66. The entrapment in PLGA microspheres of 1 to 10 microns in diameter can have an adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Thus, solid, including solid-containing-liquid, liquid, and gel (including "gel caps") compositions are envisioned.

Furthermore, the inventive constructs can be used in any desired immunization or administration regimen; e.g., as part of periodic vaccinations such as annual vaccinations as in the veterinary arts or as in periodic vaccinations as in the human medical arts, or as in a prime-boost regimen wherein an inventive construct or composition comprising a construct is administered either before or after the administration of the same or of a different epitope of interest or of a construct comprising such a same or different epitope of interest.

Furthermore, the inventive constructs can be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive individual, the reinfusion is to stimulate or boost the immune system against a pathogen.

A better understanding of the present invention and of its many advantages will be had from the following non-limiting Examples, given by way of illustration.

EXAMPLES

Example 1

Depolymerization of *Streptococcus pneumoniae*, Serotype 19F Polysaccharide Conjugate Materials used in the depolymerization process include capsular polysaccharide serotype 19F, 50 mM tris (hydroxymethyl)aminomethane prepared in sterile distilled water, 30% hydrogen peroxide, sterile 0.1N hydrochloric acid, sterile 0.1N sodium hydroxide, and sterile physiological saline (0.85%).

A one liter Wheaton Celstir™ was charged with 580 ml 50 mM tris buffer, pH 8.0. The buffer was heated to 80° C.±0.5° C. using a constant temperature recirculating water bath. When the buffer reached 80° C., 1500 mg of *Streptococcus pneumoniae* serotype 19F capsular polysaccharide was added to the heated buffer. After all of the polysaccharide dissolved (typically within 15–30 minutes), the pH was adjusted to 8.0±0.1. To this solution was added 20 ml of 30% hydrogen peroxide to give a final concentration of 1%, and the resulting mixture was stirred at 80° C. for 30 minutes. After 30 minutes, the mixture was rapidly cooled to room temperature, and the pH was adjusted to 6.0±0.5 using 0.1N HCl. The depolymerized polysaccharide was purified by ultrafiltration using a FILTRON-type minisette tangential flow filtration unit equipped with a 1,000 molecular weight cutoff (MWCO) Omega modified polyethersulfone, screen channel unit cassette. Six volumes of 0.85% saline was used to remove small molecular weight species. The depolymerized polysaccharide solution was concentrated using a FILTRON-type mini-ultrasette tangential flow filtration unit equipped with a 3,000 MWCO Omega modified polyethersulfone, screen channel unit cassette.

The molecular weight of the depolymerized polysaccharide was determined by passage through a 'gel filtration chromatography matrix sold under the trademark "SEPACRYL"' S-200 column that was previously standardized using dextran molecular weight standards. The quantity of polysaccharide recovered is determined by assaying for rhamnose (methyl pentose) using the method of Dische, Z. & Shettles, L. B. (1948) Journal of Biological Chemistry 175, pp595–603. Phosphorus content is determined by the method of Bartlett, G. R. J. (1959) Journal of Biological Chemistry, 234, 466. Reducing activity is determined by the method of Park, J. T. & Johnson, M. J. (1949) Journal of Biological Chemistry 181, pp149–151.

The polysaccharide at this stage is suitable for derivatization with an amine or hydrazide.

The inventive process is also used for capsular polysaccharide serotypes 9V and 14 derived from *Streptococcus pneumoniae* and for group A derived from *Neisseriae meningitidis*. The quantity of recovered 9V and 14 derivatized polysaccharide is determined assaying for galactose using the orcinol/sulfuric acid method of Weiner, H. E. & Moshin, J. R. (1952) American Review of Tuberculosis 68, p594. The quantity of N-acetylmannosamine in serotype 9V and the quantity of N-acetylglucosamime in serotype 14 is determined by the method of Elson, L. A. & Morgan, W. T. (1933) Biochemical Journal 27, 1824. The quantity of group A is determined by assaying for phosphorus by the method of Bartlett.

Example 2

Derivatization of *Streptococcus pneumoniae*, Serotype 19F Polysaccharide Conjugate Materials used in the derivatization process include hydrogen peroxide depolymerized capsular polysaccharide serotype 19F, from section A, adipic acid dihydrazide, EDAC, sodium cyanoborohydride, sterile 0.1N hydrochloric acid, sterile 0.1N sodium hydroxide, and sterile physiological saline, (0.85%).

A one liter beaker, equipped with a stir bar and pH probe, was charged with the concentrated depolymerized polysaccharide prepared according to Example 1, and diluted with sterile 0.85% physiological saline to achieve a final reaction concentration of 6.0 mg/ml. To this solution was added a concentrated aliquot of adipic dihydrazide and EDAC, each dissolved in sterile 0.85% physiological saline, so that each was at a final reaction concentration of 1.0 mg/ml. After EDAC was added to the reaction mixture, the pH was maintained at 5.0±0.1 for two hours using 0.1N hydrochloric acid, while keeping the reaction temperature at 22° C.±0.5° C. After two hours, a concentrated aliquot of sodium cyanoborohydride, dissolved in sterile 0.85% physiological saline, was added to the reaction mixture, so that the final reaction concentration was 2.0 mg/ml. The pH of the reaction mixture was kept at 5.0±0.1 for one hour at 22° C.±0.5° C., and the reaction was allowed to stir at the same temperature for 44 hours±4 hours. Following this reaction period, the pH was adjusted to 6.0±0.1, and the derivatized polysaccharide was purified by ultrafiltration using a FILTRON-type minisette tangential flow filtration unit, equipped with a 1,000 MWCO Omega modified polyethersulfone, screen channel unit cassette. Six volumes of 0.85% physiological saline were used to remove small molecules. The derivatized polysaccharide was concentrated using a FILTRON-type mini-ultrasette tangential flow filtration unit equipped with a 3,000 MWCO Omega modified polyethersulfone, screen channel unit cassette. The quantity of polysaccharide was determined by the methods described in Example 1. The level of hydrazide is determined by the 2,4,6-trinitrobenzesulfonic acid method of Synder, S. L. & Sobocinski, P. Z. (1975) Analytical Biochemistry 64, pp282–288.

The inventive method is also used to prepare adipic dihydrazide derivatized serotypes 9V and 14 derived from *Streptococcus pneumoniae* and for group A derived from *Neisseriae meningitidis*.

Example 3
Conjugation of *Streptococcus pneumoniae*, Serotype 19F Polysaccharide Conjugate Materials used in this preparation include adipic dihydrazide derivatized serotype 19F, prepared according to Example 2, sterile Diphtheria toxoid, EDAC, ammonium sulfate, sterile 0.1N hydrochloric acid, sterile 0.1N sodium hydroxide, and sterile physiological saline, (0.85%).

A one liter bleaker, equipped with a stir bar and pH probe, was charged with the derivatized polysaccharide from Example 2, and diluted with sterile 0.85% physiological saline to achieve a final reaction concentration of 500 nmoles reactive hydrazide/ml. To this solution was added sterile Diphtheria toxoid to a final concentration of 3.8 mg/ml. The reaction was initiated by adding a concentrated aliquot of EDAC to a final concentration of 2.25 mg/ml. The pH of the reaction mixture was adjusted to 5.0±0.1, and this pH was maintained for two hours using 0.1N hydrochloric acid. After two hours, the pH was adjusted to 7.0±0.1 using sterile 0.1N sodium hydroxide, and the reaction was stored at 5° C.±3° C. for 21 hours±3 hours.

After this period, the mixture was warmed to 22° C.±1° C., and the pH was adjusted to 6.5±0.5 using sterile 0.1N hydrochloric acid. The reaction mixture was subjected to three successive ammonium sulfate precipitations as follows. Ammonium sulfate was added as a solid to 70% saturation, and the precipitated conjugate was collected by centrifugation. The conjugate was dissolved into sterile 0.85% physiological saline, and the precipitation process was repeated. Following the third precipitation, the conjugate was diafiltered using a FILTRON-type minisette tangential flow filtration unit, equipped with a 30,000 MWCO Omega modified polyethersulfone, screen channel unit cassette. Six volumes of 0.85% physiological saline were used to remove small molecules. The diafiltered conjugate was first filtered through a filter capsule containing a 1.2 μm and a 0.45 μm filter, and then filtered through a second filter capsule containing a 0.22 μm filter. The quantity of polysaccharide determined by the methods described in Example 1. The quantity of protein is determined by the protein assay of Lowry, O. H. et. al. (1951) Journal of Biological Chemistry 193, 265–275.

The inventive process is also used to prepare polysaccharide conjugates for serotypes 9V and 14 derived from *Streptococcus pneumoniae*, and group A from *Neisseria meningitidis*.

Example 4
Depolymerization of *Streptococcus pneumoniae*, Serotype 6B Polysaccharide Conjugate Materials used in this preparation include capsular polysaccharide serotype 6B derived from *Streptococcus pneumoniae*, sterile 100 mM sodium phosphate buffer, sterile 0.1N hydrochloric acid, sterile 0.1N sodium hydroxide, 30% hydrogen peroxide, and sterile physiological saline (0.85%).

A one liter Wheaton Celstir™ was charged with 580 ml of 100 mM sodium phosphate buffer, pH 8.0. The buffer was heated to 75° C.±0.5° C. using a constant temperature recirculating water bath. When the buffer had reached 75° C.±0.5° C., 1500 mg of *Streptococcus pneumoniae* serotype 6B was added to the heated buffer. After all of the polysaccharide had dissolved, the pH of the mixture was adjusted to 8.0±0.1. To this solution was added 20 ml of 30% hydrogen peroxide to achieve a final peroxide concentration of 1%. The resulting mixture was kept at 75° C. for 25–35 minutes. Upon completion of the allotted time, the mixture was rapidly cooled to room temperature, and the pH of the mixture was lowered to 6.0±0.5 using 0.1N HCl. The depolymerized polysaccharide was purified by ultrafiltration using a Filtron minisette tangential flow filtration unit equipped with a 1000 MWCO Omega modified polyethethersulfone, screen channel unit cassette. Six volumes of 0.85% saline was used to remove small molecular weight species. The depolymerized polysaccharide solution was concentrated using a FILTRON-type mini-ultrasette tangential flow filtration unit equipped with a 3,000 MWCO Omega modified polyethersulfone, screen channel unit cassette.

Molecular weight determinations, reducing activity, phosphorus and rhamnose content were performed as in Example 1.

The inventive process was used for capsular polysaccharide serotypes 3, 4, 7F, 18C, and 23F derived from *Streptococcus pneumoniae*. The quantity of serotype 3 is determined by assaying for glucuronic acid using the method of Dische, Z. (1947) Journal of Biological Chemistry 167, p189, and the quantity of glucose is determined using the orcinol/sulfuric acid method Weiner & Moshin. The quantity of serotype 4 is determined by assaying for galactose by the orcinol/sulfuric acid method of Weiner & Moshin, the quantity of N-acetylmannosamine and N-acetylgalactosamine is determined by the Elson & Morgan method. The quantity of serotype 7F is determined by assaying for rhamnose by the Dische & Shettles method, the quantity of galactose is determined by the orcinol/sulfuric acid method of Weiner & Moshin, the quantity of N-acetylglucosamine and N-acetylgalactosamine is determined by the Elson & Morgan method. The quantity of serotype 18C is determined by assaying for rhamnose by the Dische & Shettles method, the quantity of phosphorus is determined by the Bartlett method, and the quantity of galactose is determined by the orcinol/sulfuric acid method of Weiner & Moshin. The quantity of serotype 23F is determined by assaying for rhamnose by the Dische & Shettles method, the quantity of phosphorus is determined by the Bartlett method, and the quantity of galactose is determined by the orcinol/sulfuric acid method of Weiner & Moshin. Molecular weights and reducing activity content of each of the polysaccharide listed in this example were determined by the methods described in Example 1.

Example 5
Derivation of *Streptococcus pneumoniae* Serotype 6B Polysaccharacide Conjugate The method and materials described in Example 2 is used to prepare adipic acid hydrazide derivatized serotype 6B capsular polysaccharide. These same set of reaction procedures is also used to prepare adipic acid derivatized serotypes 3, 4, 7F, 18C, and 23F capsular polysaccharide derived from *Streptococcus pneumoniae*.

Example 6
Depolymerization of *Streptococcus pneumoniae*, Serotype 6B Polysaccharide Conjugate The method and materials described in Example 3 is used to prepare serotype 6B polysaccharide conjugate. The same set of reaction procedures is also used to prepare polysaccharide conjugates of serotypes 3, 4, 7F, 18C, and 23F derived from *Streptococcus pneumoniae*.

Example 7
Depolymerization of *Neisseria meningitidis*, group A Polysaccharide Conjugate Materials used in this preparation include capsular polysaccharide group A derived from *Neisseria meningitidis*, sterile 50 mM tris buffer, sterile 0.1N hydrochloric acid, sterile 0.1N sodium hydroxide, 30% hydrogen peroxide, and sterile physiological saline (0.85%).

A one liter Wheaton Celstir™ was charged with 580 ml 50 mM citrate buffer, pH 6.0. The buffer was heated to 60° C.±0.5° C. using a constant temperature recirculating water bath. When the buffer reached 60° C., 1500 mg of group A capsular polysaccharide from *Neisseria meningitidis* was added to the heated buffer. After all of the polysaccharide dissolved, the pH was adjusted to 6.0±0.1. To this solution was added 20 ml of 30% hydrogen peroxide to give a final concentration of 1%, and the resulting mixture was stirred at 60° C. for 120 minutes.

In this Example, the reaction was run at a slow rate in order to monitor the molecular weight of the polysaccharide using an HPSEC column, in which chromatograms were taken every 15 minutes. After 120 minutes, the mixture was rapidly cooled to room temperature. The depolymerized polysaccharide was purified by ultrafiltration using a FILTRON-type minisette tangential flow filtration unit equipped with a 1,000 MWCO Omega modified polyethersulfone, screen channel unit cassette. Six volumes of 0.85% saline was used to remove small molecular weight species. The depolymerized polysaccharide solution was concentrated using a FILTRON-type mini-ultrasette tangential flow filtration unit equipped with a 3,000 MWCO Omega modified polyethersulfone, screen channel unit cassette.

Molecular weight, reducing activity, and phosphorus content were determined as described in Example 1.

Example 8
Derivatization of *Neisseria meningitidis*, group A, Polysaccharide Conjugate Materials used in this preparation include hydrogen peroxide depolymerized capsular polysaccharide group A derived from *Neisseria meningitidis*, from section A, adipic acid dihydrazide, EDAC, sodium cyanoborohydride, sulfosuccinimidyl-4(N-maleimidomethyl)cyclohexane-1-carboxylate sterile, 0.1N hydrochloric acid, sterile 0.1N sodium hydroxide, and sterile physiological saline, (0.85%).

A one liter fleaker, equipped with a stir bar and pH probe, was charged with the concentrated depolymerized polysaccharide, from section A, and diluted with sterile 0.85% physiological saline to achieve a final reaction concentration of 6.0 mg/ml. To this solution was added a concentrated aliquot of adipic dihydrazide and EDAC, each dissolved in sterile 0.85% physiological saline, so that each was at a final reaction concentration of 1.0 mg/ml. After EDAC was added to the reaction mixture, the pH was maintained at 5.0±0.1 for two hours using 0.1N hydrochloric acid, while keeping the reaction temperature at 22° C.±0.5° C. After two hours, a concentrated aliquot of sodium cyanoborohydride, dissolved in sterile 0.85% physiological saline, was added to the reaction mixture, so that the final reaction concentration was 2.0 mg/ml. The pH of the reaction mixture was kept at 5.0±0.1 for one hour at 22° C.±0.5° C., and then the reaction was allowed to stir at the same temperature for 44 hours±4 hours. Following this reaction time, the pH was adjusted to 6.0±0.1, and the derivatized polysaccharide was purified by ultrafiltration using a FILTRON-type minisette tangential flow filtration unit, equipped with a 1,000 MWCO Omega modified polyethersulfone, screen channel unit cassette. Six volumes of 0.85% physiological saline were used to remove small molecules. The derivatized polysaccharide was concentrated using a Filtron mini-ultrasette tangential flow filtration unit equipped with a 3,000 MWCO Omega modified polyethersulfone, screen channel unit cassette. The quantity of polysaccharide was determined by the methods described in section A. The level of hydrazide is determined by the 2,4,6-trinitrobenzesulfonic acid method of Synder, S. L. & Sobocinski, P. Z. (1975) Analytical Biochemistry 64, pp282–288.

A one liter fleaker, equipped with a stir bar and pH probe, was charged with the hydrazide derivatized group A polysaccharide from above, and was diluted with sterile 0.85% physiological saline to achieve a final reactive hydrazide concentration of 1000 nmoles reactive hydrazide/ml. To this solution was added solid sulfosuccinimidyl-4-(N-maleimidomethyl)cyclohexane-1-carboxylate to a final concentration of 6.6 mg/ml. The pH of the reaction mixture was adjusted to 6.5±0.1 and the reaction was stirred for 22 hours±2 hours at 22° C.±1° C. Following this reaction time, the pH was adjusted to 6.0±0.1, and the maleimido-derivatized polysaccharide was purified by ultrafiltration using a Filtron minisette tangential flow filtration unit, equipped with a 1,000 MWCO Omega modified polyethersulfone, screen channel unit cassette. Six volumes of 0.85% physiological saline was used to remove small molecules. The derivatized polysaccharide was concentrated using a FILTRON-type mini-ultrasette tangential flow filtration unit equipped with a 3,000 MWCO Omega modified polyethersulfone, screen channel unit cassette. The quantity of polysaccharide was determined by the methods described in section A. The quantity of maleimide is determined by thiol titration using Ellman's reagent.

Example 9
Conjugation of *Neisseria meningitidis*, group A Polysaccharide Conjugate Materials used in this preparation include maleimido-derivatized group A, from Example 8, sterile diphtheria toxoid, EDAC, cystamine dihydrochloride, dithiothreitol, ammonium sulfate, sterile 0.1N hydrochloric acid, sterile 0.1N sodium hydroxide, sterile physiological saline, (0.85%), and sterile 50 mM tris buffer pH 7.5, containing 0.5 mM EDTA.

A one liter fleaker, equipped with a stir bar and a pH probe, was charged with sterile diphtheria toxoid, and diluted with 0.85% physiological saline to yield a final concentration 4 mg/ml. To this solution, was added a concentrated aliquot of cystamine dihydrochloride, dissolved in 0.85% physiological saline to a final concentration of 11 mg/ml. The pH of the mixture was adjusted to pH7.0±0.1, and the reaction was initiated by adding a concentrated aliquot of EDAC to a final concentration of 2.25 mg/ml. The pH of the reaction mixture was maintained at 7.0±0.1 at 22° C.±1° C., and then was allowed to stir for 22 hours±2 hours, at the same temperature. Following this reaction, the derivatized protein was purified by ultrafiltration using a FILTRON-type minisette tangential flow filtration unit, equipped with a 10,000 MWCO Omega modified polyethersulfone, screen channel unit cassette. Six volumes of 50 mM tris pH 7.5, containing 0.5 mM EDTA was used to remove the small molecules. The quantity of protein is determined by the method of Lowry. The quantity of cyatamine is determined by either assaying for amine, or by thiol titration following reduction of the disulfide bonds using dithiothreitol.

A one liter fleaker, equipped with a stir bar and a pH probe, was charged with the cystamine derivatized diphtheria toxoid, and diluted with 50 mM tris pH 7.5, containing 0.5 mM EDTA. To this was added as a solid dithiothreitol to a final concentration of 15 mg/ml. The reaction was stirred at 22° C.±1° C. for two hours. Following this reaction period, the reduced cystamine derivatized diphtheria toxoid was purified by ultrafiltration using a Filtron minisette tangential flow filtration unit, equipped with a 10,000 MWCO Omega modified polyethersulfone, screen channel unit cassette. Six volumes of 50 mM tris pH 7.5, containing 0.5 mM EDTA was used to remove the small molecules. The quantity of protein is determined by the method of Lowry, and the quantity of thiol is determined by titration using Ellman's reagent.

A one liter fleaker, equipped with a stir bar and a pH probe, was charged with the reduced cystamine derivatized diphtheria toxoid, and diluted with 50 mM tris pH 7.5, containing 0.5 mM EDTA to a final reaction concentration of 6 mg/ml. To this solution was added a 1.5 molar excess maleimido-derivatized group A, from section B. This reaction was allowed to stir at 22° C.±1° C., for a total of 22 hours±2hours. Following this reaction period, the pH of the mixture was adjusted to 6.5±0.1, and the conjugate was purified by three successive ammonium sulfate precipitations. Following the third precipitation, the conjugate was diafiltered using a Filtron minisette tangential flow filtration unit, equipped with a 30,000 MWCO Omega modified polyethersulfone, screen channel unit cassette. Six volumes of 0.85% physiological saline were used to remove small molecules. The dialfiltered conjugate was first filtered through a filter capsule containing a 1.2 μm and a 0.45 μm filter, and then filtered through a second filter capsule containing a 0.22 μm filter. The quantity of polysaccharide is determined by phosphorus by the Bartlett method. The quantity of protein is determined by the Lowry method.

The same process is also used to prepare polysaccharide conjugates for serotypes 3, 4, 6B, 7F, 9V, 14, 18C, 19F, and 23F derived from *Streptococcus pneumoniae.*

REFERENCES

1. Dick, W. E. Jr. and Beurret, M. *Conjugate Vaccines. Contrib. Microbiol. Immunol.* (1989) 10, pp. 48–114, Cruse, J. M. and Lewis, R. E. Jr. eds. Basel, Karger.
2. Santosham, M. (1993) Vaccine 11: 552–557.
3. Isbell, H. S. and Frush, H. L. (1987) Carbohydrate Research 161: 181–193
4. Yalpani, M. *Polysaccharides Syntheses. Modifications and Structure/Property Relations* (1988) Elsevier, Amsterdam, pp. 370–388.
5. Park, J. T. and Johnson, M. J. (1949) J. Biol. Chem. 181:149.

What I claim is:

1. A method for preparing a construct comprising a polysaccharide and/or oligosaccharide covalently attached to a protein molecule, said method comprising depolymerizing and activating said polysaccharide and/or oligosaccharide using hydrogen peroxide under mild conditions, wherein said mild conditions include reaction at a temperature from about 30° C. to about 80° C. and a pH from about 4.5 to about 8.0, and wherein no metal catalysts are added;

derivatizing the depolymerized polysaccharide and/or oligosaccharide with a molecule selected from the group consisting of an amine and a hydrazide, wherein the derivatization is carried out in the presence of a carbodiimide; and conjugating said derivatized, depolymerized polysaccharide and/or oligosaccharide with a protein molecule.

2. The method of claim 1 wherein said polysaccharide is a bacterial capsular polysaccharide selected from the group consisting of *Streptococcus pneumoniae* serotypes 1, 3, 4, 5, 6B, 7F, 9V, 14, 18C, 19F and 23F and *Neisseria meningitidis* groups A,C, $14_{135}$ and Y.

3. The method of claim 1 wherein said depolymerizing is to a mean molecular weight of 10–30,000 daltons.

4. The method of claim 1 wherein said amine is 1,6-diaminohexane.

5. The method of claim 1 wherein said hydrazide is adipic dihydrazide.

6. The method of claim 1 wherein the carbodiimide is 1-Ethyl-3-(3-dimethylaminopropyl)-carbodiimide.

7. The method of claim 1 wherein said derivatized, depolymerized polysaccharide and/or oligosaccharide comprises a single selective reactive site.

8. The method of claim 7 wherein said conjugating comprises directly linking the derivatized depolymerized polysaccharide and/or oligosaccharide to a carboxylic acid group of the protein molecule.

9. The method of claim 8 wherein said conjugating additionally comprises using a water-soluble carbodiimide reagent in the presence of N-hydroxysuccinimide.

10. The method of claim 7 wherein said derivatized depolymerized polysaccharide is further derivatized with a bifunctional linker.

11. The method of claim 9 wherein the water soluble carbodiimide reagent is 1-Ethyl-3-(3-dimethylamino-propyl)-carbodiimide.

12. The method of claim 1 wherein the construct comprises moiety selected from the group consisting of an epitope of interest, a biological response modulator and a growth factor.

13. A construct prepared according to the method of claim 1.

14. A construct prepared according to the method of claim 12.

15. An immunological or therapeutic composition comprising the construct according to claim 14 and a pharmaceutically acceptable carrier or diluent, wherein the protein of said construct is capable of eliciting a T-cell dependent immune response in a host injected with said protein.

16. An immunogenic composition comprising the inmunuological composition of claim 15.

17. A method for inducing an immunological response in a vertebrate comprising administering an immunological composition of claim 15 to the vertebrate.

18. A method for treating a vertebrate in need of treatment comprising administering an immunological or therapeutic composition of claim 15 to the vertebrate.

* * * * *